United States Patent [19]
Fischer et al.

[11] Patent Number: 6,010,844
[45] Date of Patent: *Jan. 4, 2000

[54] METHODS OF PREPARING AND RECOVERING PROTEINS

[75] Inventors: Bernhard Fischer, Vienna; Artur Mitterer, Orth/Donau; Friedrich Dorner; Johann Eibl, both of Vienna, all of Austria

[73] Assignee: Baxter Aktiengesellschaft, Vienna, Austria

[ * ] Notice: This patent issued on a continued prosecution application filed under 37 CFR 1.53(d), and is subject to the twenty year patent term provisions of 35 U.S.C. 154(a)(2).

[21] Appl. No.: 08/752,892

[22] Filed: Nov. 20, 1996

[30] Foreign Application Priority Data

Nov. 24, 1995 [AT] Austria ..................................... 1927/95

[51] Int. Cl.⁷ ............................ C12Q 1/00; G01N 33/53; A61K 38/00; C07K 1/00
[52] U.S. Cl. ............................. 435/4; 435/7.1; 435/7.71; 435/7.92; 530/350; 530/344; 530/361
[58] Field of Search ..................................... 530/350, 344, 530/361; 435/4, 7.1, 7.71, 7.92

[56] References Cited

U.S. PATENT DOCUMENTS 5,053,453  10/1991  Ku ........................................... 525/54.1
5,296,352   3/1994  Schlaeppi ................................. 435/7.4

OTHER PUBLICATIONS

Burgess et al. (J. Cell Bio, 111:2129–2138), 1990.
Lazar et al. (Mol & Cell Bio, 8:1247–1252), 1998.
Tero et al (J. Immunol,143:2595–2601), 1989.

*Primary Examiner*—Paula K. Hutzell
*Assistant Examiner*—Susan Ungar
*Attorney, Agent, or Firm*—Foley & Lardner

[57] ABSTRACT

There is disclosed the preparation and recovery of proteins, in particular of enzymes, by controlled proteolytic cleavage of pro-proteins, in particular pro-enzymes, in a single method step, wherein a pro-protein-containing solution is contacted with a protease and with a solid carrier which has a higher affinity to the protein than to the pro-protein or to the functionally inactive degradation products thereof, the pro-protein being proteolytically cleaved to said protein, and the protein being selectively separated by absorption on the solid carrier.

22 Claims, 12 Drawing Sheets

Electrophoretic analysis of the digestion of rFII by trypsin (Example 1)

a: Molecular weight marker
b: Trypsin digestion, 1 minute
c: Trypsin digestion, 5 minutes Activation of rFII to rFIIa by immobilized trypsin by means of column chromatography (Example 2). Dependence of the activity of the rFIIa formed on the flow rate.

Electrophoretic assay of the protein composition of samples during the activation of rFII to rFIIa by immobilized trypsin by means of column chromatography (Example 2)

a: rFII;
b: Flow rate 1 ml/minute;
c: Flow rate 0.6 ml/minute;
d: Flow rate 0.4 ml/minute;
e: Flow rate 0.2 ml/minute;
f: Flow rate 0.1 ml/minute;
g: Flow rate 0.05 ml/minute;
h: Molecular weight marker.

Electrophoretic analysis of the activation of rFII to rFIIa by immobilized trypsin and recovery of the thrombin by affinity chromatography on hirudin-thiol-sepharose a: Starting material (rFII)
b: 1.5 M KSCN eluate (rFIIa)
c: Molecular weight marker Electrophoretic analysis of the activation of rFII to rFIIa by immobilized trypsin and recovery of the thrombin by affinity chromatography on thiol-peptide-thiol sepharose a: Molecular weight marker
b: Starting material (rFII)
c: 1.5 M KSCN eluate (rFIIa)

Electrophoretic analysis of the activation of rFII to rFIIa by immobilized trypsin and recovery of the thrombin by affinity chromatography on amino-peptide-CH sepharose a: Molecular weight marker
b: Starting material (rFII)
c: 1.5 M KSCN eluate (rFIIa)

Electrophoretic analysis of the activation of rFII to rFIIa by immobilized trypsin and recovery of the thrombin by affinity chromatography on benzamidine sepharose a: Starting material (rFII)
b: 0.1 M benzamidine eluate (rFIIa)
c: Molecular weight marker Electrophoretic analysis of the activation of rFII to rFIIa by immobilized trypsin and recovery of the thrombin by affinity chromatography on heparin sepharose a: Starting material (rFII)
b: 0.5 M NaCl eluate (rFIIa)
c: Molecular weight marker Electrophoretic analysis of the activation of rFII to rFIIa in a protein mixture by immobilized trypsin and recovery of the thrombin by affinity chromatography on amino-peptide-CH sepharose a: Starting material (protein mixture)
b: 1.5 M KSCN eluate (rFIIa)
c: Molecular weight marker

- 116,300
- 97,400

- 66,300

- 55,400

- 36,500

- 31,000

Electrophoretic analysis of the activation of hFII to FIIa by immobilized trypsin and recovery of the thrombin by affinity chromatography on benzamidine sepharose a: Molecular weight marker
b: Starting material (hFII)
c: 0.1 M benzamidine eluate (FIIa)

Electrophoretic analysis of the activation of rFII to rFIIa by immobililzed factor Xa and recovery of the thrombin by affinity chromatography on amino-peptide-CH sepharose a: Molecular weight marker
b: Starting material (rFII)

Electrophoretic analysis of the activation of FX to FXa by immobilized trypsin and recovery of FXa by affinity chromatography on benzamidine sepharose a: Starting material (FX)
b: 0.1 M benzamidine eluate (FXa)
c: Molecular weight marker

- 116,300
- 97,400

- 66,300

- 55,400

- 36,500

- 31,000

METHODS OF PREPARING AND RECOVERING PROTEINS

The invention relates to a method of preparing and recovering proteins by controlled cleavage of pro-proteins by means of a protease.

BACKGROUND OF THE INVENTION

In the living organism, a plurality of proteins and enzymes is produced by the cellulary biosynthesis as inactive pre-stages (pro-proteins (precursor proteins) or pro-enzymes). If required, these inactive pre-stages are then converted into their active forms, e.g. by limited proteolysis. Thus, in the human body, prothrombin is converted to thrombin by the protease factor Xa in a prothrombinase-complex reaction. Inactive factor X is converted to active factor Xa, by the protease factor IXa, e.g.

The recovery of the activated proteins is of major interest both for clinical applications as well as for diagnostic purposes. The activated proteins in their pure form may then, e.g., be used to control other proteolytic processes, such as the blood coagulation by thrombin in surgery, for the therapy or diagnosis or for the recovery of specific antibodies.

From living organisms, such as, e.g., human blood, the active proteins can be recovered in very limited amounts only. Therefore, the pro-proteins or pro-enzymes are mostly converted to the activated forms by the action of suitable proteases in vitro. Such a method is known from EP-0 378 798. According to this method, prothrombin derived from human plasma is adsorbed on a solid carrier, and the material is treated with $Ca^{2+}$ ions, and thereby, together with proteases present in the plasma, the conversion of prothrombin to thrombin is effected.

Another method is described in EP-A-0 565 511, in which, according to a preferred embodiment, the pro-protein to be activated is immobilized on a carrier and then is converted to the active enzyme by a soluble protease. To render this conversion controllable, it is carried out in the presence of a detergent or of a chaotropic substance. For the recovery of the activated proteins, however, further purification steps are required, in particular for separating the protease again.

According to EP-A-0 541 507, prothrombin in soluble form is converted to thrombin by adding coagulatively active salts to a prothrombin-containing solution. Subsequently, thrombin is further purified by ion exchange chromatography and/or affinity chromatography.

According to EP-A-0 565 512, thrombin is prepared by treating a prothrombin-containing solution with immobilized trypsin for 150 minutes. There, the use of the protease in the immobilized form allows for an easier separation of the protease after activation.

According to EP-A-0 416 890, recombinant human protein C (rHPC) is activated by a 2 hour treatment with thrombin immobilized on glass beads. Separation of activated rHPC from immobilized thrombin is effected by centrifugation.

When using proteases for the inactivation of pro-enzymes or pro-proteins, the problem has been encountered that the process of proteolysis does not end at the stage of the active enzymes. Rather, further peptide bonds are continued to be hydrolysed by the protease in the course of the reaction, and the activated proteins are further cleaved to low-molecular peptides that are inactive again (Kisiel and Hanahan, 1973, Biochim. Biophys. Acta 329, 221–232). Therefore, in such methods, the yield is known to be low, when activating prothrombin to thrombin by trypsin, e.g., the yield is only 50% (Kisiel and Hanahan, 1973, Biochim. Biophys. Acta 329, 221–232).

Attempts have been made to improve such methods by adding stabilizers, such as albumin or glycine, to the activating reaction, so as to reduce the further degradation of the activated proteins (Landaburu et al. 1961, Am. J. Physiol. 201, 298–302).

However, a substantial disadvantage of these methods consists in that, although at a slower pace, a further degradation to protein fragments does occur, and protein mixtures form which additionally contain large amounts of additives, such as detergents or glycerol. Therefore, complex methods of purifying the activated enzymes are necessary.

Protein fragments and detergents or chaotropic substances were removed according to EP-A-0 565 511 by relatively complex chromatographic methods.

SUMMARY OF THE INVENTION

Thus the present invention has as an object to provide a method of preparing proteins from pro-proteins, by which a high yield of proteins can be attained and which enables the recovery of proteins with a very high specific activity and purity in a simple manner. The method shall not be restricted to certain starting solutions but shall be applicable to a wide spectrum of starting solutions.

According to the invention, this object is achieved by a method of preparing and recovering proteins by controlled proteolytic cleavage of pro-proteins by means of a protease, which is characterized in that a pro-protein-containing solution is contacted with a protease and a solid carrier that has a higher affinity to the protein than to the pro-protein or to the functionally inactive degradation products thereof, the pro-protein being proteolytically cleaved to protein, and the protein being selectively separated by adsoption on the solid carrier. Preferably, an immobilized protease is used. It offers the advantage that it can be separated easily from the solution.

The pro-protein-containing solution is treated with the protease for a period of contact sufficient to cause a cleavage of the pro-protein to protein, in which, however, substantially no further functionally inactive degradation products of the protein are formed.

The invention also provides methods of preparing and recovering a protein, comprising the step of contacting a pro-protein of a protein with a protease and solid carrier, wherein (i) the protease cleaves the pro-protein to form the protein and degradation products, and (ii) the solid carrier has an affinity to the protein that exceeds the affinity of the solid carrier to the pro-protein and the degradation products so as to selectively adsorb the protein on the solid carrier. The method also can comprise the step of recovering the protein from the solid carrier. The solid carrier can comprises at least one selected from the group consisting of hirudin, hirudin derivative, polypeptides, and benzamidine.

The protease according to the invention can be immobilized. The pro-protein can be contacted with the protease for a time period between about 1 second to about 24 hours or more.

According to the invention, the protease can be selected from the group consisting of trypsin, chymotrypsin, factor Xa, venom-protease, thrombin, plasmin and a serine-protease of the subtilisin family The serine-protease can be a kexin-type protease or a furin-type protease.

The pro-protein can be a pro-enzyme and the protein can an enzyme. The pro-protein can be an inactive pre-stage of a blood clotting factor and the protein can be a functionally active clotting factor For example, the blood-clotting factor can be selected from the group consisting of factor II, factor V, factor VII, factor VIII, pro-factor IX, factor IX, factor X, factor XIII, protein C and von Willebrand factor.

The pro-protein can be obtained from any source, including plasma, a plasma fraction, a plasma-derived solution and a culture supernatant derived from a recombinant cell culture. The pro-protein can be in a purified form or accompanied by other proteins.

It has been shown that the time during which the protease acts on the pro-protein is an important factor for the quality of the protein to be produced, and that keeping a specified period of contact between protease/pro-protein under certain parameters is important for the preparation of a defined protein. The period of contact must be chosen such that the conversion of the pro-protein to the protein does take place, yet that a further undesired degradation of the protein can no longer take place, but the action of the protease is prevented before that.

Critical parameters for determining the optimum period of contact thus are the protease used, the ratio of pro-protein to protease and the reaction temperature. According to the method of the invention, any skilled artisan may easily determine and optimize the critical parameters before the reaction is started, in case they are not already known from the prior art.

The period of contact specific to the preparation of a specified protein may be determined in each case by simply varying the period of contact in separate experimental set-ups. In each case, the products obtained are analysed, and subsequently that period of contact by which a maximum of the desired protein and a minimum of further degradation products or non-cleaved pro-protein can be obtained is defined as the given period of contact.

This given period of contact naturally will be different from system (pro-protein/protease) to system, in many systems, however, it will be less than 24 hours. Periods of time of between 1 second and 24 hours, in particular between 1 second and 5 hours, more particular between 1 second and 30 minutes, have proved to be the preferred periods of action for the protease.

As an additional measure according to the invention, to keep the period of contact of the action of the protease as exact as possible and to prevent the further degradation of the protein, directly upon the protease treatment, the protein formed by the protease is bound to a carrier that has a higher affinity to the protein than to the pro-protein or to the functionally inactive degradation products thereof. Thus, the protein is withdrawn from further action by the protease in the reaction mixture, and a further degradation of the protein can no longer occur.

This is, e.g., possible by providing the affinity carrier for the protein in the pro-protein or protease containing solution, or by arranging two chromatographic columns in series, the (immobilized) protease being in the first column and the solid carrier for the protein being in the second colum, the eluate from the first column getting directly to the head of the second column. According to a preferred embodiment of the method according to the invention—if the protease treatment has not been quantitative—the non-cleaved pro-protein that has remained in the solution may again be contacted with the (immobilized) protease in a recycling process, cleaved, and the protein formed may be bound to the selective carrier. This may, e.g., be effected by connecting the outlet of the second, selective carrier with the first, protease-coupled column, the non-bound pro-protein again being made accessible to the action of the protease. These steps may be repeated until substantially the entire pro-protein has been cleaved to protein.

In addition to the preferred, continuous carrying out of the protease treatment step(s) and the adsorption step(s), it is, of course, also possible to carry out this method discontinuously, in that the (immobilized) protease and the highly selective carrier for the protein formed are in one and the same container, and, if two different solid carriers are being used, one of the two solid carriers may be removed selectively (e.g. by binding either protease or protein to a magnetic surface or to a removable insert).

The method according to the invention can, of course, be used for all protease-mediated conversions of pro-proteins to proteins, preferably it is used for preparing enzymes from pro-enzymes.

For the proteolytic cleavage of pro-proteins, a plurality of proteases is suitable, e.g. chymotrypsin, dispase, endopeptidase Arg-C, endoproteinase Lys-C, endoproteinase Glu-C, endoproteinase Asp-N, factor Xa, Kallikrein, papain, pepsin, plasmin, pronase, proteinase K, staphylocoagulase, serine proteases of the subtilisin family, such as, e.g., kexin-tpye or furin-type proteases, or subtilisin, thrombin, trypsin (in particular human, bovine, porcine), trypsin-type protease from arthropodes or micro-organism, such as Streptomyces griseus-trypsin or serine proteases from venomous snakes (Venom-proteases), such as, e.g., the prothrombin activators of Echis carinatus Venom and from Oxyuranus scutellatus Venom; the activators of factor X and factor V from Russel's Viper Venom, or the protein C activator agkistrodon contortrix Venom. Trypsin, chymotrypsin, Kallikrein, dispase, endoproteinases Glu-C, Lys-C or Asp-N, furin or factor Xa are preferably utilized as the protease. Also recombinant proteases may, of course, be used.

As has been mentioned, the protease is preferably immobilized on a solid carrier so that the protease can at no time react in soluble form with the pro-protein or the protein formed. To immobilize the protease, in particular cellulose, SEPHAROSE (beaded agarose), dextrane, agarose, acrylate or silikate are suitable as natural or synthetic carriers.

According to a preferred embodiment of the invention usable by way of routine, the immobilized protease (the protease gel) is packed into a glass column, and the pro-protein containing solution is filtered through the protease gel. The flow rate is chosen such that the given period of contact between the immobilized protease and the pro-protein is kept.

According to this embodiment, the thus activated protein is adsorbed directly from the desorption supernatant (eluate) on a selective carrier. With a view to a purposeful recovery of the desired protein with high purity and in high yields, non-activated pro-protein should not be bound by the specific carrier, if possible, and should freely pass the column comprising the selective carrier. For a further activation, this pro-protein containing fraction is again contacted for the specified period of contact with the protease gel, whereupon further protein is formed, which then again is adsorbed from the solution by the selective carrier. By the continuous controlled activation on the protease gel and elution, as well as by the immediate adsorption of the activated protein on the selective second carrier, the pro-protein is completely converted to activated protein without activated protein being further cleaved by the protease. Activated protein accumulates on the selective carrier and subsequently can be eluted from the carrier.

Particularly preferred proteins which may be prepared by the method according to the invention are functionally active blood clotting enzymes derived from the inactive pre-stages of these enzymes by proteolytic degradation. According to the invention, e.g., thrombin can be prepared from prothrombin (factor II), factor IX from pro-factor IX, factor IXa from factor IX, von Willebrand factor from pro-von Willebrand factor, factor Xa from factor X, activated protein C from protein C, factor XIIIa from factor XIII, factor VIIa from factor VII, factor VIIIa from factor VIII, factor Va from factor V.

In the method according to the invention, the starting solutions (pro-protein containing solutions) are not limited to any particularly prepared solutions. Yet, preferred pro-protein containing solutions comprise the pro-protein in purified form, since then a particularly pure protein preparation becomes possible.

Pro-protein containing solutions comprising the pro-protein admixed with other proteins are, however, also suitable for the method according to the invention, because on account of its high specificity, contaminating proteins are not a significant disturbing factor for the method according to the invention.

Thus, preferably, pro-protein containing solutions of biological origin, in particular plasma or solutions derived from plasma or from plasma fractions, are used in the present method.

According to a further preferred embodiment of the method according to the invention, biotechnologically prepared pro-protein containing solutions, in particular culture supernatants prepared from recombinant cell cultures are used as the starting solutions.

Heparin immobilized on a matrix, immobilized benzamidine, immobilized hirudin or fractions and derivatives derived from hirudin, various immobilized proteins or peptides, in particular specific immobilized antibodies, are particularly suitable as selective solid carriers for the proteins to be prepared and to be adsorbed thereon in the activated state.

The protein preferably is selectively eluted from the affinity carriers, so that any other proteins that might possibly also be bound, even though in slight amounts, (specifically or unspecifically) to the carrier are separated.

To inactivate infectious agents, in particular human pathogenic viruses, possibly present, additional virus inactivating measures generally known from the prior art can be carried out within the scope of the method according to the invention.

According to another aspect, the present invention relates to the use of the method according to the invention for the preparation of proteins from pro-proteins, preferably of activated enzymes from pro-enzymes, in particular for the preparation of activated factor II, of activated factor V, of activated factor VII, of activated factor VIII, of factor IX, of activated factor IX, of activated factor X, of activated factor XIII, of von Willebrand factor and of activated protein C.

On account of its high purity and its high specific activity, the protein containing fraction obtained by the method according to the invention is excellently suitable for preparing a pharmaceutical preparation and, starting from the eluted protein, may be processed by the usual methods into such a pharmaceutical preparation. A further aspect of the invention thus relates to pharmaceutical compositions comprising a highly purified protein prepared according to the method of the invention, in particular factor IIa, factor Va, factor VIIa, factor VIIIa, factor IX, factor IXa, factor Xa, factor XIIIa, activated protein C and/or von Willebrand factor, as well as optionally one or several physiologically acceptable carriers and/or other pharmaceutical additives.

The choice of the selective solid carrier for the protein formed is of great importance in the method of the invention. Immobilized hirudin and polypeptides and fragments derived therefrom have proved to be particularly preferred carriers (in particular when preparing factor IIa).

Thus, the invention also relates to hirudin and polypeptides and peptide fragments or derivatives derived therefrom which are immobilized on a solid surface. Peptides derived from hirudin which come from the C-terminal region of the protein and contain the thrombin binding site have proved as particularly suitable in this connection. According to the invention, the peptides chosen are preferably coupled to the carrier via sulfur or amino groups.

According to a preferred embodiment of the invention, both purified human factor II from plasma (prothrombin, Stago Diagnostica), and purified recombinant factor II (Falkner, F. G., et al., Thromb. Haemost. (1992), 68, 119–124), a factor II-containing protein mixture (Falkner, F. G., et al., Thromb. Haemost. (1992), 68, 119–124) and purified factor X (Boehringer Mannheim) are used as pro-protein containing solution. Preferably both immobilized trypsin and immobilized factor Xa are preferably used therein as the protease.

According to a further aspect, the invention also relates to a protein complex which contains a protein adsorbed on a solid carrier, prepared according to the method of the invention, in particular to a thrombin complex that contains thrombin which is adsorbed on a solid carrier, preferably on a solid carrier containing hirudin or fragments or derivatives derived from hirudin.

Still a further aspect of the present invention relates to an apparatus arrangement comprising a container (I) containing a protease, and a container (II) containing a solid carrier, wherein (I) and (II) are directly connected, which apparatus arrangement is used to carry out the method of the invention, preferably the single-stage embodiment thereof.

Preferably, the containers (I) and (II) are columns, the end portion of (I) being directly coupled to the head portion of (II) and optionally the end portion of (II) being connected with the head portion of (I).

The invention will now be explained in more detail by way of the following Examples and the associated drawing figures to which, however, it shall not, be restricted.

DETAILED DESCRIPTION OF PREFERRED EMBODIMENTS

EXAMPLES

Figure 1:
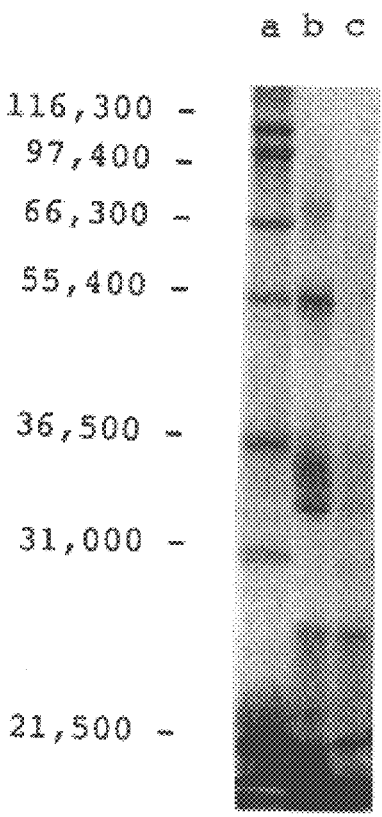
FIG. 1 shows the electrophoretic analysis of the proteolysis products of recombinant factor II (rFII) by trypsin according to Example 1.

Activity Determinations:

The activity determination of factor IIa (FIIa) was carried out photometrically in 50 mM Tris-HCl buffer, pH 8.0, 300 mM NaCl, 0.5% albumin, 7.5 mM EDTA, at 37° C. The FIIa specific chromogenic substrate AcOH-H-D-CHG-Ala-Arg-pNA (obtainable from Pentapharm) at a concentration of 0.2 mM was used as the substrate. para-Nitroanilin (pNA) released from the substrate by enzymatic hydrolysis was photometrically determined in dependence on the time at 405 nm. By using a FIIa concentration standard (of Immuno AG), the activity of the sample was determined from the speed of the hydrolysis of the substrate.

The activity determination of factor Xa (FXa) was effected photometrically in 50 mM Tris-HCl buffer, pH 7.8, 0.5% albumin, at 37° C. The FXa-specific chromogenic substrate Bz-Ile-Glu(piperidyl)-Gly-Arg-pNA (SEQ ID NO: 1) (obtainable from Chromogenix) at a concentration of 0.3 mM was used as the substrate. pNA released from the substrate by enzymatic hydrolysis was photometrically determined in dependence on the time at 405 nm. By using an FXa concentration standard (of Immuno AG), the activity of the sample was determined from the speed of the hydrolysis of the substrate.

The protein determination for natural factor II and recombinant factor II (FII/rFII) and for FIIa/rFIIa, respectively, was effected by measuring the absorption at 280 nm by using the extinction coefficient (1%, 1 cm) of 13.8 and 17.9, respectively (Human Protein Data, Ed. by A. Haeberli, VCH Weinheim, New York, 1992).

The protein determination for FX and FXa, respectively, was effected by measuring the absorption at 280 nm by using an extinction coefficient (1%, 1 cm) of 12.4 (Human Protein Data, Ed. by A. Haeberli, VCH Weinheim, New York, 1992).

The determination of the protein concentrations of protein mixtures was effected by means of the Bradford method (M. Bradford, Anal. Biochem., 72 (1976), 248–254) by using a commercially available system of Bio-Rad.

Example 1

Activation of prothrombin to thrombin by immobilized trypsin in dependence on the period of contact between protease and pro-protein 4 ml of recombinant prothrombin (recombinant factor II, rFII) at a concentration of 0.5 mg/ml (activity 4 I.U. FII/ml) in 20 mM Tris/HCl buffer, pH 8.0, 150 mM NaCl, were admixed with 0.1 ml of immobilized trypsin-agarose gel (Sigma, USA; 80 units of trypsin/ml gel) and stirred at room temperature. Samples were taken after 1 min and after 5 min and assayed for their content of recombinant thrombin (recombinant factor IIa, rFIIa) (for data, cf. Table 1).

TABLE 1

| Sample | rFIIa activity (I.U./ml) |
| --- | --- |
| starting sample | — |
| rFII, 0.4 mg/ml, 4 ml | 500 |
| trypsin digestion 1 minute | |
| rFIIa, 0.4 mg/ml, 4 ml | |
| trypsin digestion 5 minutes | 40 |
| rFIIa, 0.4 mg/ml, 4 ml | |

The samples obtained were assayed for their protein composition by means of denaturing electrophoresis (Laemmli, Nature, Vol. 227:680–685, (1970)). The results are illustrated in FIG. 1, the molecular weight marker being illustrated in lane a, the 1-minute trypsin digestion being illustrated in lane b, and the 5-minute trypsin digestion being illustrated in lane c.

From these results there follows that rFII was converted to rFIIa by the digestion with trypsin. After as little as 1 minute of trypsin action on rFII with an activity of 4 I.U./ml, rFIIa was formed therefrom with an activity of 500 I.U./ml. Yet at a period of action of 5 minutes, the detectable activity of rFIIa was very low. Electrophoretic analysis shows that a trypsin action on rFII of 1 minute only, a protein mixture having molecular weights (in Da) of between 70000 and 20000 is present, a protein having the molecular mass of between 31000 and 36000 being dominant. Since, as is known, thrombin has a molecular mass of 33000 in electrophoresis, it may be assumed that the protein having the molecular mass of 31000–36000 is thrombin that has formed. However, residues of non-activated rFII (molecular weight 70000) are also still present. However, when incubating rFII with trypsin for 5 minutes, only low-molecular peptides were detected in the electrophoresis. This suggests a nearly complete digestion of the rFII by trypsin, yet without rFIIa accumulating.

Example 2

Activation of recombinant prothrombin to thrombin by immobilized trypsin

Figure 2:
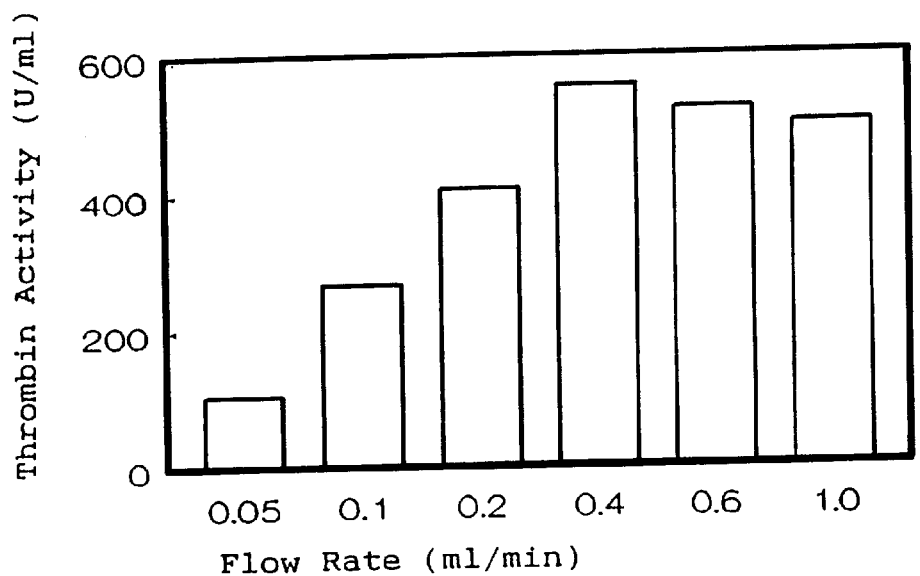
FIG. 2 shows the dependence of the activity of rFIIa formed in U/ml on the flow rate (ml/min)

A glass column (diameter 1 cm) was filled with 0.1 ml of immobilized trypsin-agarose gel; this corresponds to a gel height of 1.25 mm. rFII was pumped at different flow rates through this trypsin-agarose gel. rFII was dissolved at 0.5 mg/ml (3.5 I.U./ml) in 20 mM Tris/HCl buffer, pH 8.0, 150 mM NaCl. The flow rate of the rFII solution through the gel was varied between 0.05 ml/minute and 1.0 ml/minute. The individual eluates were assayed for their content of thrombin activity (cf. FIG. 2) and for their protein composition by means of electrophoresis (cf. FIG. 3). From the flow rates and the dimension of the trypsin-agarose gel column (volume, 0.1 ml gel; diameter of the column, 1 cm; layer thickness, 1.25 mm) there result average periods of contact of 6 seconds, 10 seconds, 15 seconds, 30 seconds, 60 seconds and 120 seconds at corresponding flow rates of 1.0 ml/minute, 0.6 ml/minute, 0.4 ml/minute, 0.2 ml/minute. 0.1 ml/minute and 0.05 ml/minute, between rFII and the immobilized trypsin.

Figure 3:
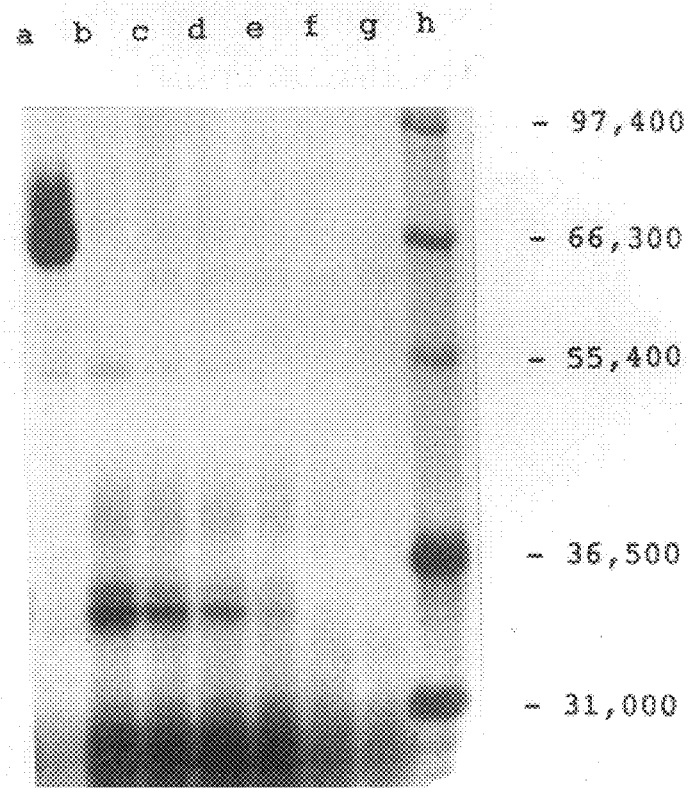
FIG. 3 shows the results from an electrophoretic assay of the activation of FII to FIIa with immobilized trypsin.

The electrophoretic lanes illustrated in FIG. 3 were loaded with the following samples:
a: rFII;
b: flow rate 1 ml/min;
c: flow rate 0.6 ml/min;
d: flow rate 0.4 ml/min;
e: flow rate 0.2 ml/min;
f: flow rate 0.1 ml/min;
g: flow rate 0.05 ml/min;
h: molecular weight marker.

From the results there follows that the formation of rFIIa from rFII by trypsin digestion depends very much on the flow rate, i.e. on the period of contact between rFII and immobilized trypsin. The highest activities of rFIIa were achieved with a flow rate of 0.4 ml/minute. At higher flow rates (0.6 ml/minute and 1 ml/minute), the yields of rFIIa decrease again. Electrophoresis shows that at these flow rates, not the entire rFII was proteolytically converted to rFIIa by trypsin. At lower flow rates (0.05 ml/min to 0.2 ml/min), the amount of rFIIa also decreases. The electrophoretic assay shows that only slight amounts of active thrombin accumulate on account of the increased periods of contact between rFII and immobilized trypsin, and with a decreasing flow rate, inactive, low-moleular peptides form.

Example 3

Activation of recombinant prothrombin to thrombin by immobilized trypsin, and recovery of the thrombin by affinity chromatography on hirudin-thiol sepharose.

4000 antithrombin units (ATU) of hirudin (obtainable from Pentapharm) were reduced, and subsequently they were coupled to 1 ml of activated thiol-sepharose (Pharmacia) according to the producer's instructions. Hirudin-thiol sepharose (HTS) was filled into a glass column (diameter 1 cm).

The outlet of a glass column (diameter 1 cm) which contained 0.1 ml of immobilized trypsin-agarose gel (TAG) was connected with the inlet of the HTS column by a direct hose connection. The outlet of the HTS column was connected with the inlet of the TAG column via a valve and a pump, whereby a liquid circulation was formed. Both columns were equilibrated with 20 mM Tris/HCl buffer, pH 8.0.

rFII was dissolved at 0.4 mg/ml (activity: 3.5 I.U./ml) in 4 ml 20 mM Tris/HCl buffer, pH 8.0, and pumped through the TAG column at a flow rate of 0.8 ml/min. From there, the liquid flow was directly guided to the HTS column without interruption, and after passage of the HTS column, it was pumped for a second time through the TAG column and the HTS column by means of a pump. Subsequently, the HTS column was separated from the TAG column, flushed with 50 mM citrated buffer, pH 6.5 (to remove material that had not been bound) and then washed with 50 mM Na citrated buffer, pH 6.5, 500 mM NaCl (0.5 M NaCl eluate). Subsequently, the HTS column was eluted with 1.5 M KSCN in 50 mM citrated buffer, pH 6.5 (1.5 M KSCN eluate).

The fractions obtained during activation were assayed for thrombin activity (I.U./ml), total activity (I.U.) and specific activity (thrombin activity/mg protein). In Table 2, the results of the rFII activation from Example 3 are listed.

TABLE 2

| Sample | rFIIa Activity (I.U./ml) | rFIIa Activity (I.U. total) | rFIIa Specific Activity (I.U./mg protein) |
|---|---|---|---|
| Starting material | 0 | 0 | 0 |
| Non-bound material | 0 | 0 | 0 |
| 0.5 M NaCl eluate | 50 | 100 | 300 |
| 1.5 M KSCN eluate | 390 | 2150 | 3400 |

Figure 4:
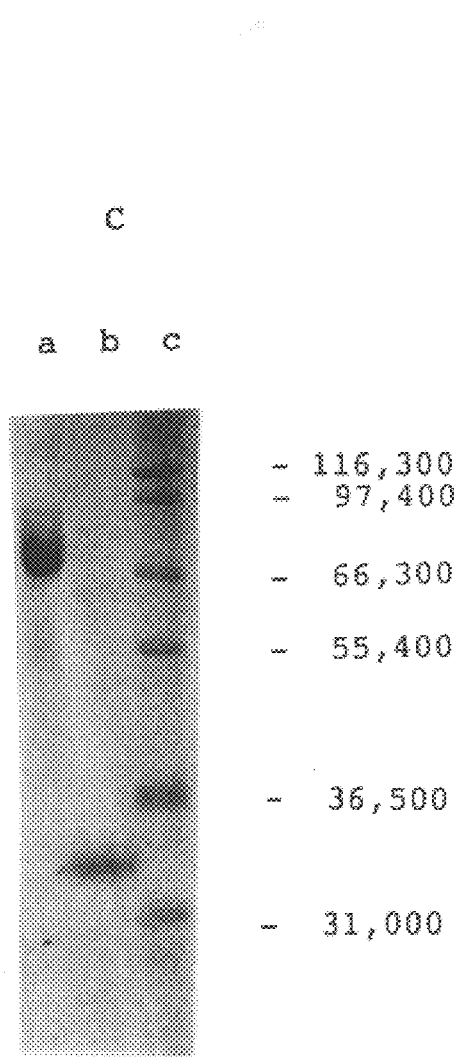
FIG. 4 shows the results from an electrophoretic assay of the activation of FII to FIIa with immobilized trypsin and the recovery of FIIa by affinity chromatography on hirudin-thiol-sepharose.

FIG. 4 shows the electrophoretic assay of the activation described, wherein in lane a the starting material (rFII), in lane b the 1.5 M KSCN eluate (rFIIa) and in lane c a molecular weight marker has been separated.

The results show that by the method described in Example 3, rFII was effectively converted to rFIIa. rFIIa formed accumulated on the HTS column and was obtained in electrophoretically pure form with a molecular weight of 33000 and with a very high specific activity by specific elution of the HTS column. More than 150 I.U. of pure rFIIa could be recovered from 1 I.U. of rFII by the method described. This corresponds to a substantially quantitative conversion.

Example 4

Activation of recombinant prothrombin to thrombin by immobilized trypsin, and recovery of the thrombin by affinity chromatography on thiol-peptid-thiol sepharose.

20 mg of a peptide (thiol peptide, TP) having the amino acid sequence $NH_2$-Cys-Lys-Pro-Gln-Ser-His-Asn-Asp-Gly-Asp-Phe-Glu-Glu-Ile-Pro-Glu-Glu-Tyr-Leu-Gln-COOH (SEQ ID NO: 2) were coupled to 1 ml of activated thiol sepharose (obtainable from Pharmacia) according to the producer's instructions. Thiol-peptide-thiol sepharose (TPTS) was filled into a glass column (diameter 1 cm). The outlet of a glass column (diameter 1 cm) which contained 0.1 ml immobilized trypsin-agarose gel (TAG) was connected via a direct hose connection with the inlet of the TPTS column. The outlet of the TPTS column was connected with the inlet of the TAG column via a valve and a pump, whereby a liquid circulation was formed. Both columns were equilibrated with 20 mM Tris/HCl buffer, pH 8.0.

rFII was dissolved at 0.4 mg/ml (activity 3.5 I.U./ml) in 4 ml 20 mM Tris/HCl buffer, pH 8.0, and pumped through the TAG column at a flow rate of 0.8 ml/min. From there, the liquid flow was directly guided to the TPTS column without interruption, and after passage of the TPTS column, it was pumped for a second time through the TAG column and the TPTS column by means of a pump. Subsequently, the TPTS column was separated from the TAG column, flushed with 50 mM citrated buffer, pH 6.5 (to remove material that had not been bound) and then washed with 50 mM Na citrated buffer, pH 6.5, 500 mM NaCl (0.5 M NaCl eluate). Subsequently, the TPTS column was eluted with 1.5 M KSCN in 50 mM citrated buffer, pH 6.5 (1.5 M KSCN eluate). The fractions obtained during activation were assayed for thrombin activity (I.U./ml), total activity (I.U.) and specific activity (thrombin activity/mg protein). In Table 3, the results of the rFII activation obtained are listed.

TABLE 3

| Sample | rFIIa Activity | | rFIIa Specific Activity |
|---|---|---|---|
| | (I.U./ml) | (I.U. total) | (I.U./mg protein) |
| Starting material | 0 | 0 | 0 |
| Non-bound material | 0 | 0 | 0 |
| 0.5 M NaCl eluate | 45 | 100 | 300 |
| 1.5 M KSCN eluate | 380 | 2250 | 3250 |

Figure 5:
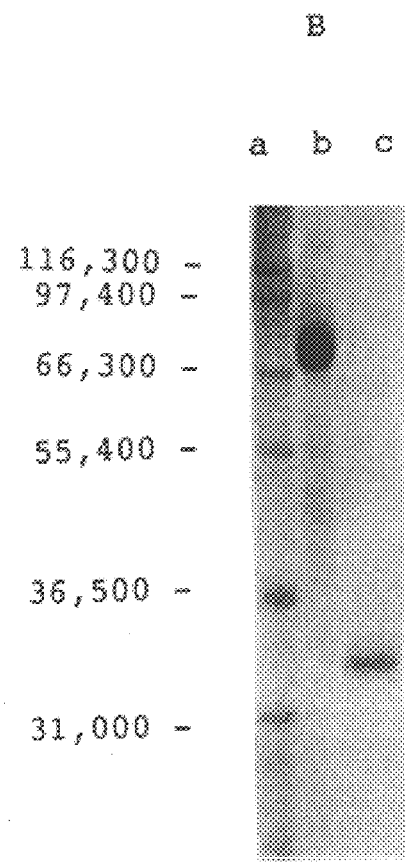
FIG. 5 shows the results from an electrophoretic assay of the activation of FII to FIIa with immobilized trypsin and the recovery of FIIa by affinity chromatography on thiol-peptide-thiol sepharose.

FIG. 5 shows the electrophoretic analysis of the activation of rFII to rFIIa by immobilized trypsin and the recovery of the thrombin by affinity chromatography on thiol-peptide-thiol sepharose, wherein in lane a the molecular weight marker, in lane b the starting material (rFII) and in lane c the 1.5 M KSCN eluate (rFIIa) have been applied.

The results show that by the method described, rFII was effectively converted to rFIIa. rFIIa formed accumulated on the TPTS column and was obtained in electrophoretically pure form with a molecular weight of 33000 and with a very high specific activity by specific elution of the TPTS column. More than 150 I.U. of pure rFIIa could be recovered from 1 I.U. of rFII by the method described.

Example 5

Activation of recombinant prothrombin to thrombin by immobilized trypsin, and recovery of the thrombin by affinity chromatography on amino-peptide-CH sepharose.

20 mg of a peptide (amino peptide, AP) having the amino acid sequence $NH_2$-Lys-Pro-Gly-Pro-Gly-Ser-His-Ala-Asp-Gly-Asp-Phe-Glu-Glu-Ile-Pro-Glu-Glu-Tyr-Leu-COOH (SEQ ID NO: 3) were coupled to 1 ml of activated CH sepharose (Pharmacia) according to the producer's instructions. Amine-peptide-CH sepharose (APCHS) was filled into a glass column (diameter 1 cm). The outlet of a glass column (diameter 1 cm) which contained 0.1 ml immobilized trypsin-agarose gel (TAG) was connected via a direct hose connection with the inlet of the APCHS column. The outlet of the APCHS column was connected with the inlet of the TAG column via a valve and a pump, whereby a liquid circulation was formed. Both columns were equilibrated with 20 mM Tris/HCl buffer, pH 8.0.

rFII was dissolved at 0.4 mg/ml (activity 3.5 I.U./ml) in 4 ml 20 mM Tris/HCl buffer, pH 8.0, and pumped through the TAG column at a flow rate of 0.8 ml/min. From there, the liquid flow was directly guided to the APCHS column without interruption, and after passage of the APCHS column, it was pumped for a second time through the TAG column and the APCHS column by means of a pump. Subsequently, the APCHS column was separated from the TAG column, flushed with 50 mM citrated buffer, pH 6.5 (whereby material that had not been bound was removed) and then washed with 50 mM Na citrated buffer, pH 6.5, 500 mM NaCl (0.5 M NaCl eluate). Subsequently, the APCHS column was eluted with 1.5 M KSCN in 50 mM citrated buffer, pH 6.5 (1.5 M KSCN eluate). The fractions obtained during activation were assayed for thrombin activity (I.U./ml), total activity (I.U.) and specific activity (thrombin activity/mg protein). In Table 4, the results of the rFII activation obtained are listed.

TABLE 4

| Sample | rFIIa Activity | | rFIIa Specific Activity |
|---|---|---|---|
| | (I.U./ml) | (I.U. total) | (I.U./mg protein) |
| Starting material | 0 | 0 | 0 |
| Non-bound material | 0 | 0 | 0 |
| 0.5 M NaCl eluate | 55 | 110 | 280 |
| 1.5 M KSCN eluate | 320 | 2400 | 3500 |

Figure 6:
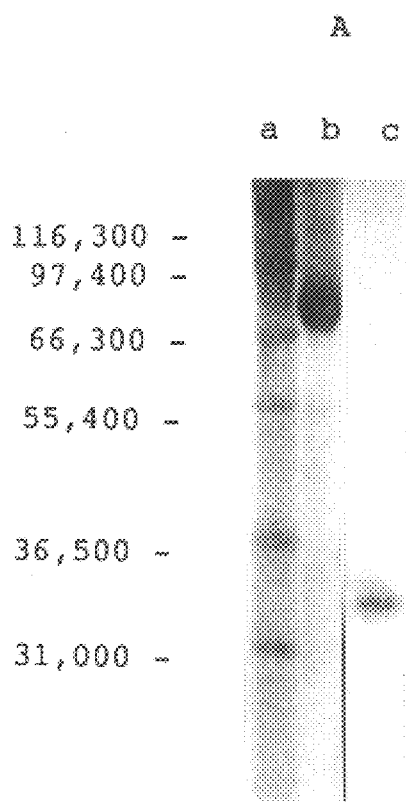
FIG. 6 shows the results from an electrophoretic assay of the activation of FII to FIIa with immobilized trypsin and the recovery of FIIa by affinity chromatography on amino-peptide-CH sepharose.

FIG. 6 shows the electrophoretic analysis of the activation of rFII to rFIIa by immobilized trypsin and the recovery of the thrombin by affinity chromatography on amino-peptide-CH sepharose, wherein in lane a the molecular weight marker, in lane b the starting material (rFII) and in lane c the 1.5 M KSCN eluate (rFIIa) have been separated.

The results show that by the method described in Example 5, rFII was effectively converted to rFIIa. rFIIa formed accumulated on the APCHS column and was obtained in electrophoretically pure form with a molecular weight of 33000 and with a very high specific activity by specific elution of the APCHS column. More than 150 I.U. of pure rFIIa could be recovered from 1 I.U. of rFII by the method described.

Example 6

Activation of recombinant prothrombin to thrombin by immobilized trypsin, and recovery of the thrombin by affinity chromatography on benzamidine sepharose 2 ml benzamidine sepharose (BAS, Pharmacia) were filled into a glass column (diameter 1 cm). The outlet of a glass column (diameter 1 cm) which contained 0.1 ml of immobilized trypsin-agarose gel (TAG) was connected with the inlet of the BAS column by a direct hose connection. The outlet of the BAS column was connected with the inlet of the TAG column via a valve and a pump, whereby a liquid circulation was formed. Both columns were equilibrated with 20 mM Tris/HCl buffer, pH 8.0.

rFII was dissolved at 0.4 mg/ml (activity: 3.5 I.U./ml) in 4 ml 20 mM Tris/HCl buffer, pH 8.0, and pumped through the TAG column at a flow rate of 0.8 ml/min. From there, the liquid flow was directly guided to the BAS column without interruption, and after passage of the BAS column, it was pumped for a second time through the TAG column and the BAS column by means of a pump. Subsequently, the BAS column was separated from the TAG column, flushed with 50 mM citrated buffer, pH 6.5 (to remove material that had not been bound) and then washed with 50 mM Na citrated buffer, pH 6.5, 150 mM NaCl (0.15 M NaCl eluate). Subsequently, the BAS column was eluted with 0.1 M benzamidine in 50 mM citrated buffer, pH 6.5 (0.1 M benzamidine eluate). The fractions obtained during activation were assayed for thrombin activity (I.U./ml), total activity (I.U.) and specific activity (thrombin activity/mg protein). In Table 5, the results of the rFII activation are listed.

TABLE 5

| | rFIIa Activity | | rFIIa Specific Activity |
|---|---|---|---|
| Sample | (I.U./ml) | (I.U. total) | (I.U./mg protein) |
| Starting material | 0 | 0 | 0 |
| Non-bound material | 0 | 0 | 0 |
| 0.15 M NaCl eluate | 0 | 0 | 0 |
| 0.1 M benzamidine eluate | 670 | 2100 | 360 |

TABLE 6

| | rFIIa Activity | | rFIIa Specific Activity |
|---|---|---|---|
| Sample | (I.U./ml) | (I.U. total) | (I.U./mg protein) |
| Starting material | 0 | 0 | 0 |
| Non-bound material | 1 | 10 | 5 |
| 0.15 M NaCl eluate | 0 | 0 | 0 |
| 0.1 M NaCl eluate | 400 | 2110 | 2670 |

Figure 7:
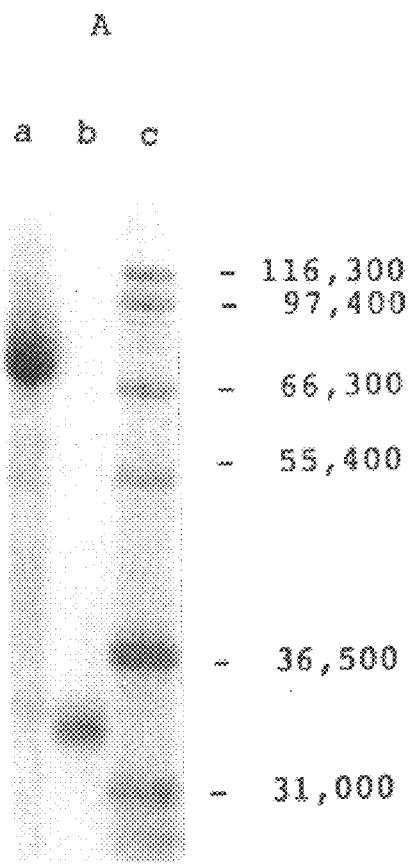
FIG. 7 shows the results from an electrophoretic assay of the activation of FII to FIIa with immobilized trypsin and the recovery of FIIa by affinity chromatography on benzamidine sepharose.

FIG. 7 shows the electrophoretic analysis of the activation of rFII to rFIIa by immobilized trypsin and the recovery of the thrombin by affinity chromatography on benzamidine sepharose, wherein in lane a the starting material (rFII), in lane b the 0.1 M benzamidine eluate (rFIIa) and in lane c a molecular weight marker have been applied.

The results show that by the method described in Example 6, rFII was effectively converted to rFIIa. rFIIa formed accumulated on the BAS column and was obtained in electrophoretically pure form with a molecular weight of 33000 and with a very high specific activity by specific elution of the BAS column. More than 150 I.U. of pure rFIIa could be recovered from 1 I.U. of rFII by the method described.

Example 7

Activation of recombinant prothrombin to thrombin by immobilized trypsin, and recovery of the thrombin by affinity chromatography on heparin sepharose.

2 ml of Heparin-Sepharose Fast Flow (HS, Pharmacia) were filled into a glass column (diameter 1 cm). The outlet of a glass column (diameter 1 cm) which contained 0.1 ml of immobilized trypsin-agarose gel (TAG) was connected with the inlet of the HS column by a direct hose connection. The outlet of the BAS column was connected with the inlet of the TAG column via a valve and a pump, whereby a liquid circulation was formed. Both columns were equilibrated with 20 mM Tris/HCl buffer, pH 8.0. rFII was dissolved at 0.4 mg/ml (activity: 3.5 I.U./ml) in 4 ml 20 mM Tris/HCl buffer, pH 8.0, and pumped through the TAG column at a flow rate of 0.8 ml/min. From there, the liquid flow was directly guided to the HS column without interruption, and after passage of the HS column, it was pumped for a second time through the TAG column and the HS column by means of a pump. Subsequently, the HS column was separated from the TAG column, flushed with 50 mM citrated buffer, pH 6.5 (to remove material that had not been bound) and then washed with 50 mM Na citrated buffer, pH 6.5, 150 mM NaCl (0.15 M NaCl eluate). Subsequently, the HS column was eluted with 0.5 M NaCl in 50 mM citrated buffer, pH 6.5 (0.5 M NaCl eluate). The fractions obtained during activation were assayed for thrombin activity (I.U./ml), total activity (I.U.) and specific activity (thrombin activity/mg protein). In Table 6, the results of the rFII activation from Example 7 are listed.

Figure 8:
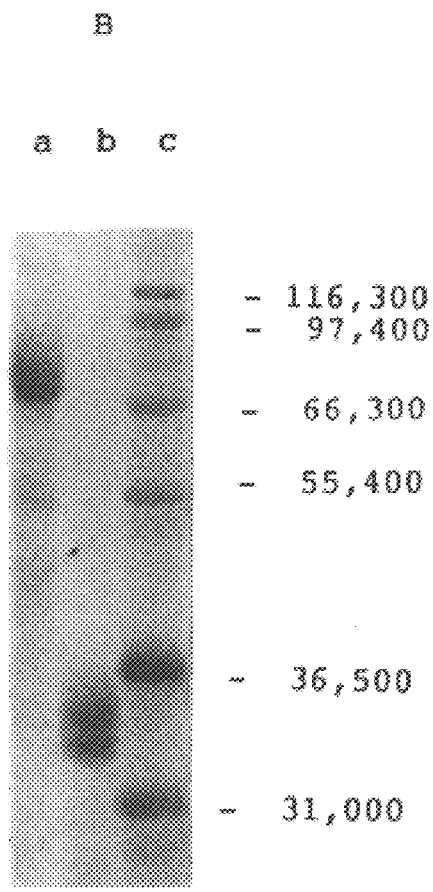
FIG. 8 shows the results from an electrophoretic assay of the activation of FII to FIIa with immobilized trypsin and the recovery of FIIa by affinity chromatography on heparin sepharose.

FIG. 8 shows the electrophoretic analysis of the activation of rFII to rFIIa by immobilized trypsin and the recovery of the thrombin by affinity chromatography on heparin sepharose, wherein in lane a the starting material (rFII), in lane b the 0.5 M NaCl eluate (rFIIa) and in lane c the molecular weight marker have been applied.

The results show that by the method described in Example 7, rFII was effectively converted to rFIIa. rFIIa formed accumulated on the HS column and was obtained in electrophoretically pure form with a molecular weights of 33000 and 35000 and with a very high specific activity by specific elution of the HS column. More than 150 I.U. of pure rFIIa could be recovered from 1 I.U. of rFII by the method described.

Example 8

Activation of recombinant prothrombin to thrombin in a protein mixture by immobilized trypsin, and recovery of the thrombin by affinity chromatography on amino-peptide-CH sepharose.

An amino-peptide-CH sepharose column (APCHS column) was prepared as described in Example 5. The outlet of a glass column (diameter 1 cm) which contained 0.1 ml of immobilized trypsin-agarose gel (TAG) was connected with the inlet of the APCHS column by a direct hose connection. The outlet of the APCHS column was connected with the inlet of the TAG column via a valve and a pump, whereby a liquid circulation was formed. Both columns were equilibrated with 20 mM Tris/HCl buffer, pH 8.0.

4 ml of a protein mixture (protein concentration 1.7 mg/ml) which contained rFII (activity 3.5 I.U./ml) in 20 mM Tris/HCl buffer, pH 8.0, were pumped through the TAG column at a flow rate of 0.8 ml/min. From there, the liquid flow was directly guided to the APCHS column without interruption, and after passage of the APCHS column, it was pumped for a second time through the TAG column and the APCHS column by means of a pump. Subsequently, the APCHS column was separated from the TAG column, flushed with 50 mM citrated buffer, pH 6.5 (to remove material that had not been bound) and then washed with 50 mM Na citrated buffer, pH 6.5, 500 mM NaCl (0.5 M NaCl eluate). Subsequently, the APCHS column was eluted with 1.5 M KSCN in 50 mM citrated buffer, pH 6.5 (1.5 M KSCN eluate). The fractions obtained during activation were assayed for thrombin activity (I.U./ml), total activity (I.U.) and specific activity (thrombin activity/mg protein). In Table 7, the results of the rFII activation from Example 8 are listed.

TABLE 7

| Sample | rFIIa Activity | | rFIIa Specific Activity |
|---|---|---|---|
| | (I.U./ml) | (I.U. total) | (I.U./mg protein) |
| Starting material | 0 | 0 | 0 |
| Non-bound material | 0 | 0 | 0 |
| 0.5 M NaCl eluate | 44 | 120 | 230 |
| 1.5 M KSCN eluate | 305 | 2250 | 3300 |

Figure 9:
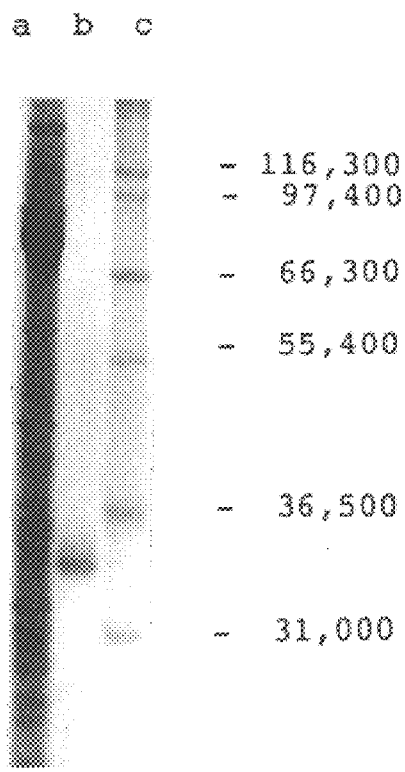
FIG. 9 shows the results from an electrophoretic assay of the activation of FII to FIIa in a protein mixture with immobilized trypsin and the recovery of FIIa by affinity chromatography on amino-peptide-CH sepharose.

FIG. 9 shows the electrophoretic analysis of the activation of rFII to rFIIa in a protein mixture by immobilized trypsin and the recovery of the thrombin by affinity chromatography on amino-peptide-CH sepharose, wherein in lane a the starting material (protein mixture), in lane b the 1.5 M KSCN eluate (rFIIa) and in lane c a molecular weight marker have been applied.

The results show that by the method described in Example 8, in a protein mixture rFII was effectively converted to rFIIa. rFIIa formed accumulated on the APCHS column and was obtained in electrophoretically pure form with a molecular weight of 33000 and with a very high specific activity by specific elution of the APCHS column. More than 150 I.U. of pure rFIIa could be recovered from 1 I.U. of rFII by the method described.

Example 9

Activation of human prothrombin to thrombin by immobilized trypsin, and recovery of the thrombin by affinity chromatography on benzamidine sepharose.

2 ml of benzamidine sepharose (BAS, Pharmacia) were filled into a glass column (diameter 1 cm). The outlet of a glass column (diameter 1 cm) which contained 0.1 ml of immobilized trypsin-agarose gel (TAG) was connected with the inlet of the BAS column by a direct hose connection. The outlet of the BAS column was connected with the inlet of the TAG column via a valve and a pump, whereby a liquid circulation was formed. Both columns were equilibrated with 20 mM Tris/HCl buffer, pH 8.0.

Human Factor II (hFII) was dissolved at 0.5 mg/ml (activity: 4 I.U./ml) in 4 ml 20 mM Tris/HCl buffer, pH 8.0, and pumped through the TAG column at a flow rate of 0.8 ml/min. From there, the liquid flow was directly guided to the BAS column without interruption, and after passage of the BAS column, it was pumped for a second time through the TAG column and the BAS column by means of a pump. Subsequently, the BAS column was separated from the TAG column, flushed with 50 mM citrated buffer, pH 6.5 (whereby material that had not been bound was removed) and then washed with 50 mM Na citrated buffer, pH 6.5, 150 mM NaCl (0.15 M NaCl eluate). Subsequently, the BAS column was eluted with 0.1 M benzamidine in 50 mM citrated buffer, pH 6.5 (0.1 M benzamidine eluate). The fractions obtained during activation were assayed for thrombin activity (I.U./ml), total activity (I.U.) and specific activity (thrombin activity/mg protein). In Table 8, the results of the hFII activation from Example 9 are listed.

TABLE 8

| Sample | hFIIa Activity | | hFIIa Specific Activity |
|---|---|---|---|
| | (I.U./ml) | (I.U. total) | (I.U./mg protein) |
| Starting material | 0 | 0 | 0 |
| Non-bound material | 0.5 | 3 | 1.7 |
| 0.15 M NaCl eluate | 0 | 0 | 0 |
| 0.1 M benzamidine eluate | 491 | 2450 | 3270 |

Figure 10:
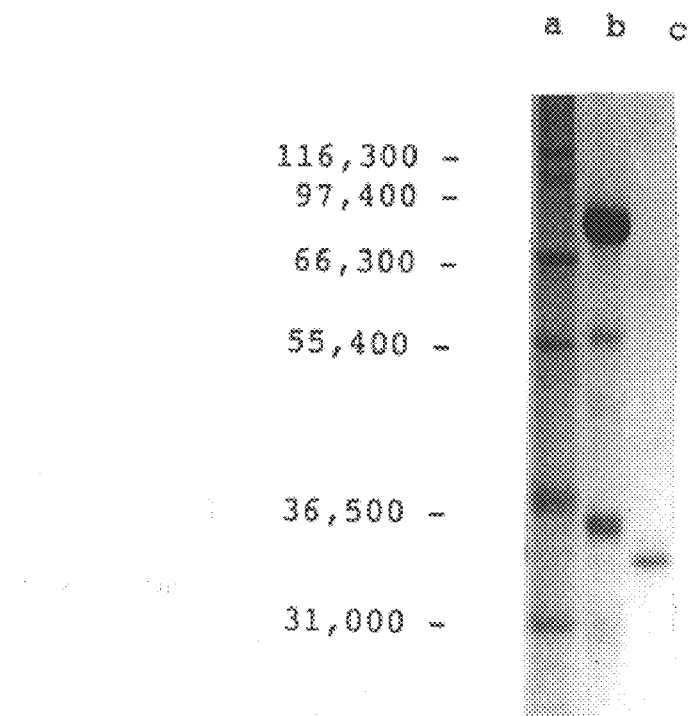
FIG. 10 shows the results from an electrophoretic assay of the activation of hFII to FIIa with immobilized trypsin and the recovery of FIIa by affinity chromatography on benzamidine sepharose.

FIG. 10 shows the electrophoretic analysis of the activation of hFII to FIIa by immobilized trypsin and the recovery of the thrombin by affinity chromatography on benzamidine sepharose, wherein in lane a the molecular weight marker, in lane b the starting material (hFII), and in lane c the 0.1 M benzamidine eluate (FIIa) have been applied.

The results show that by the method described in Example 9, hFII was effectively converted to FIIa. FIIa formed accumulated on the BAS column and was obtained in electrophoretically pure form with a molecular weight of 33000 and with a very high specific activity by specific elution of the BAS column. More than 150 I.U. of pure FIIa could be recovered from 1 I.U. of hFII by the method described.

Example 10

Activation of recombinant prothrombin to thrombin by immobilized factor Xa, and recovery of the thrombin by affinity chromatography on amino-peptide-CH sepharose.

An amino-peptide-CH-sepharose column (APCHS-column) was prepared as described in Example 5. 30 mg of the protease factor Xa (Boehringer Mannheim) were coupled to 1 ml of CNBr-activated sepharose (Pharmacia) according to the producer's instructions and filled into a glass column (diameter 1 cm) (XaS-column). The outlet of the XaS-column was connected with the inlet of the APCHS column by a direct hose connection. The outlet of the APCHS column was connected with the inlet of the XaS column via a valve and a pump, whereby a liquid circulation was formed. Both columns were equilibrated with 20 mM Tris/HCl buffer, pH 8.0.

rFII was dissolved at 0.4 mg/ml (activity: 3.5 I.U./ml) in 4 ml 20 mM Tris/HCl buffer, pH 8.0, and pumped through the XaS column at a flow rate of 0.1 ml/min. From there, the liquid flow was directly guided to the APCHS column without interruption, and after passage of the APCHS column, it was pumped for a second time through the XaS column and the APCHS column by means of a pump. This procedure was repeated for three more times. Subsequently, the APCHS column was separated from the XaS column, flushed with 50 mM citrated buffer, pH 6.5 (to remove non-bound material) and then washed with 50 mM Na citrated buffer, pH 6.5, 500 mM NaCl (0.5 M NaCl eluate). Subsequently, the APCHS column was eluted with 1.5 M KSCN in 50 mM citrated buffer, pH 6.5 (1.5 M KSCN eluate). The fractions obtained during activation were assayed for thrombin activity (I.U./ml), total activity (I.U.) and specific activity (thrombin activity/mg protein). In Table 9, the results of the rFII activation from Example 10 are summarized.

TABLE 9

| Sample | rFIIa Activity | | rFIIa Specific Activity |
|---|---|---|---|
| | (I.U./ml) | (I.U. total) | (I.U./mg protein) |
| Starting material | 0 | 0 | 0 |
| Non-bound material | 0 | 0 | 0 |
| 0.5 M NaCl eluate | 35 | 80 | 80 |
| 1.5 M KSCN eluate | 30 | 2230 | 3050 |

Figure 11:
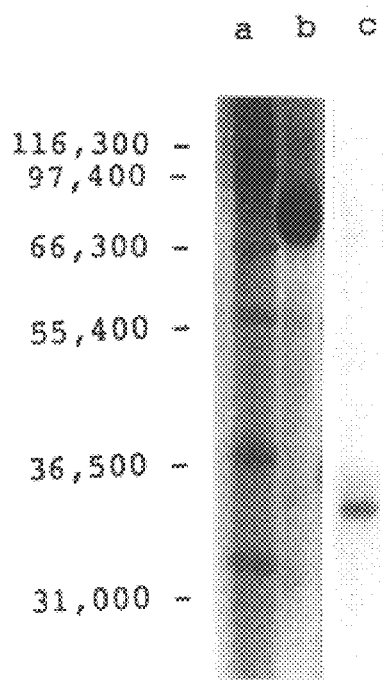
FIG. 11 shows the results from an electrophoretic assay of the activation of rFII to rFIIa with immobilized factor Xa and the recovery of FIIa by affinity chromatography on amino-peptide-CH sepharose.

FIG. 11 shows the electrophoretic analysis of the activation of rFII to rFIIa by immobilized factor Xa and the recovery of the thrombin by affinity chromatography on amino-peptide-CH sepharose, wherein in lane a the molecular weight marker, in lane b the starting material (rFII), and in lane c the 1.5 M KSCN eluate (rFIIa) have been applied.

The results show that by the method described in Example 10, rFII was effectively converted by the protease factor Xa to rFIIa. FIIa formed accumulated on the APCHS column and was obtained in electrophoretically pure form with a molecular weight of 33000 and with a very high specific activity by specific elution of the APCHS column. More than 150 I.U. of pure rFIIa could be recovered from 1 I.U. of rFII by the method described.

Example 11

Activation of factor X to factor Xa by immobilized trypsin, and recovery of the factor Xa by affinity chromatography on benzamidine sepharose.

2 ml of benzamidine sepharose (BAS, Pharmacia) were filled into a glass column (diameter 1 cm). The outlet of a glass column (diameter 1 cm) which contained 0.1 ml of immobilized trypsin-agarose gel (TAG) was connected with the inlet of the BAS column by a direct hose connection. The outlet of the BAS column was connected with the inlet of the TAG column via a valve and a pump, whereby a liquid circulation was formed. Both columns were equilibrated with 20 mM Tris/HCl buffer, pH 8.0.

2 ml of a solution of factor X (FX, of Boehringer Mannheim) were dissolved at 0.5 mg/ml in 20 mM Tris/HCl buffer, pH 8.0, and pumped through the TAG column at a flow rate of 0.5 ml/min. From there, the liquid flow was directly guided to the BAS column without interruption, and after passage of the BAS column, it was pumped for a second time through the TAG column and the BAS column by means of a pump. Subsequently, the BAS column was separated from the TAG column, flushed with 50 mM citrated buffer, pH 6.5 (to remove non-bound material) and then washed with 50 mM Na citrated buffer, pH 6.5, 150 mM NaCl (0.15 M NaCl eluate). Subsequently, the BAS column was eluted with 0.1 M benzamidine in 50 mM citrated buffer, pH 6.5 (0.1 M benzamidine eluate). The fractions obtained during activation were assayed for factor Xa activity (I.U./ml), total activity (I.U.) and specific activity (activity/mg protein). In Table 10, the results of the factor X activation from Example 11 are listed.

TABLE 10

| Sample | FXa Activity | | FXa Specific Activity |
|---|---|---|---|
| | (I.U./ml) | (I.U. total) | (I.U./mg protein) |
| Starting material | 0 | 0 | 0 |
| Non-bound material | 20 | 100 | 30 |
| 0.15 M NaCl eluate | 0 | 0 | 0 |
| 0.1 M benzamidine eluate | 520 | 1560 | 2600 |

Figure 12:
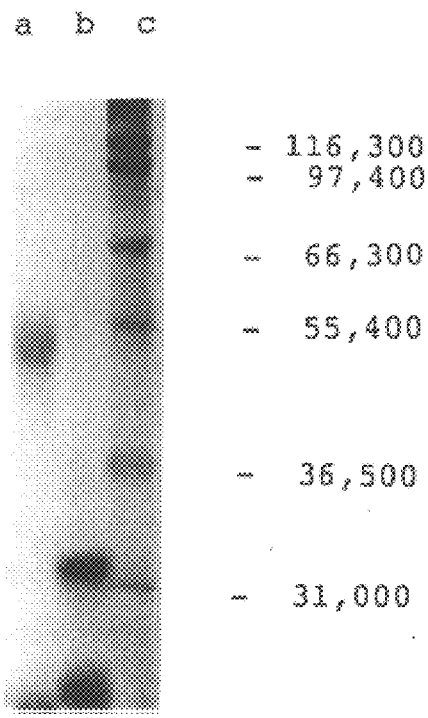
FIG. 12 shows the results from an electrophoretic assay of the activation of FX to FXa with immobilized trypsin and the recovery of FXa by affinity chromatography on benzamidine sepharose.

FIG. 12 shows the electrophoretic analysis of the activation of FX to FXa by immobilized trypsin and the recovery of the FXa by affinity chromatography on benzamidine sepharose, wherein in lane a the starting material (FX), in lane b the 0.1 M benzamidine eluate (FXa), and in lane c the molecular weight marker have been applied.

The results show that by the method described in Example 11, FX was effectively converted to FXa. FXa formed accumulated on the BAS column and was obtained in electrophoretically pure form with a molecular weight of 32000 and with a very high specific activity by specific elution of the BAS column.

It is to be understood that the description, specific examples and data, while indicating exemplary embodiments, ar given by way of illustration and are not intended to limit the present invention. Various changes and modifications within the present invention will become apparent to the skilled artisan from the discussion, disclosure and data contained herein.

What is claimed is:

1. A method of preparing and recovering a protein from a pro-protein solution, comprising
   providing a pro-protein-containing solution, wherein the pro-protein is selected from the group consisting of factor II, factor V, factor VII, factor VIII, pro-factor IX, factor IX, factor X, factor XIII, protein C and pro-von Willebrand factor;
   providing a protease selected from the group consisting of trypsin, chymotrypsin, factor Xa, venom-protease, thrombin, plasmin and a serine-protease of the subtilisin family;
   providing a solid carrier selected from the group consisting of immobilized hirudin, hirudin derivatives shown in the sequence of SEQ ID NO 2 and SEQ ID NO:3, immobilized heparin, immobilized benzamidine, immobilized antibodies, and immobilized peptides, wherein said solid carrier has a higher affinity to said protein to be recovered than to the pro-protein and to degradation products;
   contacting said pro-protein-containing solution with said protease and said solid carrier so as to proteolytically cleave said pro-protein to said protein, wherein said contacting of said pro-protein-containing solution with said protease is effected for a period of time sufficient to cleave said pro-protein to said protein, and wherein no further degradation of said protein takes place; and
   selectively separating said protein by adsorbing said protein on said solid carrier.

2. A method according to claim 1, wherein said serine-protease of said subtilisin family is selected from the group consisting of kexin-type proteases and furin-type proteases.

3. A method according to claim 1, wherein said pro-protein is an inactive pre-stage of a blood clotting factor and said protein is the functionally active clotting factor thereof.

4. A method according to claim 1, wherein the pro-protein is in a purified form.

5. A method according to claim 1, wherein said pro-protein containing solution is admixed with other proteins.

6. A method according to claim 1, wherein said pro-protein-containing solution is a solution of biological origin.

7. A method according to claim 1, wherein said pro-protein-containing solution is selected from the group consisting of plasma, a plasma fraction and a solution derived therefrom.

8. A method according to claim 1, wherein said pro-protein-containing solution is a culture supernatant prepared from a recombinant cell culture.

9. A method according to claim 1, wherein said solid carrier is a highly selective solid carrier, and further comprising selectively eluting said protein adsorbed on said solid carrier from said solid carrier.

10. A method of preparing and recovering a protein, comprising the step of:
    contacting (A) a pro-protein selected from the group consisting of factor II, factor V, factor VII, factor VIII, pro-factor IX, factor IX, factor X, factor XIII, protein C and pro-von Willebrand factor with (B) a protease selected from the group consisting of trypsin, chymotrypsin, factor Xa, venom-protease, thrombin, plasmin and a serine-protease of the subtilisin family and (C) a solid carrier selected from the group consisting of immobilized hirudin, hirudin derivatives shown in the sequence of SEQ ID NO 2 and SEQ ID NO:3, immobilized heparin, immobilized benzamidine, immobilized antibodies, and immobilized peptides, wherein (i) the protease cleaves the pro-protein to form the protein and degradation products, and (ii) the solid carrier has an affinity to the protein that exceeds the affinity of the solid carrier to the pro-protein and the degradation products so as to selectively adsorb the protein on the solid carrier wherein said contacting of said pro-protein with said protease is effected for a period of time sufficient to cleave said pro-protein to said protein, and wherein no further degradation of said protein takes place, and recovering the protein from the carrier.

11. A method according to claim 10, wherein the protease is immobilized.

12. A method according to claim 10, wherein the pro-protein is an inactive pre-stage of a blood clotting factor and the protein is the functionally active clotting factor.

13. A method according to claim 10, wherein the pro-protein is in a purified form.

14. A method according to claim 10, wherein the pro-protein is admixed with other proteins.

15. A method according to claim 10, wherein the pro-protein is obtained from one of the group consisting of plasma, a plasma fraction and a plasma-derived solution.

16. A method according to claim 10, wherein the pro-protein is obtainable from a culture supernatant derived from a recombinant cell culture.

17. A hirudin derivative immobilized on a gel matrix, wherein the hirudin derivative consists of Cys-Lys-Pro-Gln-Ser-His-Asn-Asp-Gly-AsP-Phe-Glu-Glu-Ile-Pro-Glu-Glu-Tyr-Leu-Gln, SEQ ID NO:2.

18. A hirudin derivative according to claim 17, wherein the gel matrix is beaded agarose.

19. A hirudin derivative immobilized on a gel matrix, wherein the hirudin derivative consists essentially of Lys-Pro-Gly-Pro-Gly-Ser-His-Ala-Asp-Gly-Asp-Phe-Glu-Glu-Ile-Pro-Glu-Glu-Tyr-Leu, SEQ ID NO:3.

20. A hirudin derivative according to claim 19, wherein the gel matrix is beaded agarose.

21. A method of preparing and recovering a protein, comprising the step of:

contacting (A) a pro-protein selected from the group consisting of factor II, factor V, factor VII, factor VIII, pro-factor IX, factor IX, factor X, factor XIII, protein C and pro-von Willebrand factor with (B) an immobilized protease selected from the group consisting of trypsin, chymotrypsin, factor Xa, venom-protease, thrombin, plasmin and a serine-protease of the subtilisin family and C) a solid carrier selected from the group consisting of immobilized hirudin, hirudin derivatives shown in the sequence of SEQ ID NO 2 and SEQ ID NO:3 according to SEQ ID NO: 2 or SEQ ID NO: 3, immobilized heparin, immobilized benzamidine, immobilized antibodies, and immobilized peptides, wherein (i) the immobilized protease cleaves the pro-protein to form the protein and degradation products, wherein the protease is immobilized on a material selected from the group consisting of cellulose, sepharose, dextran, agarose, acrylate and silicate, and (ii) the solid carrier has an affinity to the protein that exceeds the affinity of the solid carrier to the pro-protein and the degradation products so as to selectively adsorb the protein on the solid carrier wherein said contacting of said pro-protein with said protease is effected for a period of time sufficient to cleave said pro-protein to said protein, and wherein no further degradation of said protein takes place, and recovering the protein from the carrier.

22. The method according to claim 21, wherein the immobilized protease is packed on a gel column.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:1:

Ile Glu Gly Arg
1

(2) INFORMATION FOR SEQ ID NO:2:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:2:

```
Cys Lys Pro Gln Ser His Asn Asp Gly Asp Phe Glu Glu Ile Pro Glu
1               5                   10                  15

Glu Tyr Leu Gln
            20
```

(2) INFORMATION FOR SEQ ID NO:3:

(i) SEQUENCE CHARACTERISTICS:
        (A) LENGTH: 20 amino acids
        (B) TYPE: amino acid
        (D) TOPOLOGY: linear (ii) MOLECULE TYPE: peptide (xi) SEQUENCE DESCRIPTION: SEQ ID NO:3:

```
Lys Pro Gly Pro Gly Ser His Ala Asp Gly Asp Phe Glu Glu Ile Pro
1               5                   10                  15

Glu Glu Tyr Leu
            20
```